US011058572B2

(12) United States Patent
Kostic et al.

(10) Patent No.: US 11,058,572 B2
(45) Date of Patent: Jul. 13, 2021

(54) THERMAL CONTROL SYSTEM

(71) Applicant: Stryker Corporation, Kalamazoo, MI (US)

(72) Inventors: Marko N. Kostic, Portage, MI (US); Gregory S. Taylor, Kalamazoo, MI (US); Andrew M. Bentz, Kalamazoo, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 273 days.

(21) Appl. No.: 15/729,173

(22) Filed: Oct. 10, 2017

(65) Prior Publication Data

US 2018/0098878 A1      Apr. 12, 2018

Related U.S. Application Data

(60) Provisional application No. 62/406,676, filed on Oct. 11, 2016.

(51) Int. Cl.
*A61F 7/00*        (2006.01)
*A61F 7/02*        (2006.01)
(Continued)

(52) U.S. Cl.
CPC .......... *A61F 7/0053* (2013.01); *A61F 7/0085* (2013.01); *A61F 7/02* (2013.01);
(Continued)

(58) Field of Classification Search
CPC .................................................. C02F 2103/42
See application file for complete search history.

(56) References Cited

U.S. PATENT DOCUMENTS 3,625,279 A    12/1971  Mayo et al.
3,872,726 A     3/1975  Kauffeld et al.
(Continued)

FOREIGN PATENT DOCUMENTS

EP       0448414 B1    10/1994
EP       2514453 A1    10/2012
(Continued)

OTHER PUBLICATIONS

Gaymar Medi-Therm III, Hyper/Hypothermia Machine Ref MTA7912 Service Manual, Nov. 2009.
(Continued)

*Primary Examiner* — Dirk R Bass
(74) *Attorney, Agent, or Firm* — Warner Norcross + Judd LLP (57) ABSTRACT

A thermal control unit for delivering temperature-controlled fluid to one or more patient pads that are in contact with a patient is disclosed. The thermal control unit includes a fluid circuit with an inlet and outlet, a heat exchanger, a pump, and a controller. A fluid quality monitor is included in some embodiments to monitor a cleanliness of the circulating fluid and issue an alert if the cleanliness falls below a threshold. A valve may be included that is controlled by the controller based upon a measurement of the cleanliness of the circulating fluid and/or the passage of a predetermined amount of time. A second valve may also be included in some embodiments that selectively diverts fluid to an additional filter. The additional filter is used to determine if a cleaning action taken with respect to the circulating fluid was effective or not.

17 Claims, 7 Drawing Sheets

(51) Int. Cl.
  *B01D 29/56*     (2006.01)
  *B01D 29/60*     (2006.01)
  *B01D 29/90*     (2006.01)
  *B01D 35/143*    (2006.01)
  *C02F 1/00*      (2006.01)
  *C02F 1/50*      (2006.01)
  *C02F 103/02*    (2006.01)

(52) U.S. Cl.
  CPC ......... *B01D 29/56* (2013.01); *B01D 29/608* (2013.01); *B01D 29/902* (2013.01); *B01D 35/143* (2013.01); *C02F 1/001* (2013.01); *C02F 1/008* (2013.01); *C02F 1/50* (2013.01); *A61F 2007/0054* (2013.01); *C02F 2103/026* (2013.01); *C02F 2201/005* (2013.01); *C02F 2209/02* (2013.01); *C02F 2209/03* (2013.01); *C02F 2303/04* (2013.01)

(56) References Cited

U.S. PATENT DOCUMENTS

| | | | |
|---|---|---|---|
| 3,894,213 A | 7/1975 | Agarwala | |
| 3,995,621 A | 12/1976 | Fletcher et al. | |
| 4,149,529 A | 4/1979 | Copeland et al. | |
| 4,224,154 A * | 9/1980 | Steininger | C02F 1/008 |
| | | | 137/93 |
| 4,459,468 A | 7/1984 | Bailey | |
| 4,547,977 A | 10/1985 | Tenedini et al. | |
| 4,680,445 A | 7/1987 | Ogawa | |
| 4,691,762 A * | 9/1987 | Elkins | A61F 7/02 |
| | | | 165/46 |
| 4,707,587 A | 11/1987 | Greenblatt | |
| 4,844,072 A | 7/1989 | French et al. | |
| 5,197,537 A | 3/1993 | Chigira et al. | |
| 5,381,954 A | 1/1995 | Tokizaki | |
| 5,486,207 A | 1/1996 | Mahawili | |
| 5,562,604 A | 10/1996 | Yablon et al. | |
| 5,634,940 A | 6/1997 | Panyard | |
| 5,711,155 A | 1/1998 | De Vilbiss et al. | |
| 5,759,162 A | 6/1998 | Oppelt et al. | |
| 5,862,675 A | 1/1999 | Scaringe et al. | |
| 5,865,841 A | 2/1999 | Kolen et al. | |
| 5,871,526 A | 2/1999 | Gibbs et al. | |
| 5,894,615 A | 4/1999 | Alexander | |
| 5,895,418 A | 4/1999 | Saringer | |
| 5,948,012 A | 9/1999 | Mahaffey et al. | |
| 5,980,561 A | 11/1999 | Kolen et al. | |
| 6,086,609 A | 7/2000 | Buckley | |
| 6,091,060 A | 7/2000 | Getchel et al. | |
| 6,188,930 B1 | 2/2001 | Carson | |
| 6,197,045 B1 | 3/2001 | Carson | |
| 6,231,594 B1 | 5/2001 | Dae | |
| 6,290,717 B1 | 9/2001 | Philips | |
| 6,338,727 B1 | 1/2002 | Noda et al. | |
| 6,350,276 B1 | 2/2002 | Knowlton | |
| 6,352,550 B1 | 3/2002 | Gildersleeve et al. | |
| 6,375,674 B1 | 4/2002 | Carson | |
| 6,451,209 B1 * | 9/2002 | Kaas | C02F 1/32 |
| | | | 210/650 |
| 6,461,379 B1 | 10/2002 | Carson et al. | |
| 6,551,348 B1 | 4/2003 | Blalock et al. | |
| 6,620,187 B2 | 9/2003 | Carson et al. | |
| 6,620,188 B1 | 9/2003 | Ginsburg et al. | |
| 6,645,232 B2 | 11/2003 | Carson | |
| 6,648,905 B2 | 11/2003 | Hoglund et al. | |
| 6,660,027 B2 | 12/2003 | Gruszecki et al. | |
| 6,669,715 B2 | 12/2003 | Hoglund et al. | |
| D487,147 S | 2/2004 | Ellingboe et al. | |
| 6,692,518 B2 | 2/2004 | Carson | |
| 6,695,874 B2 | 2/2004 | Machold et al. | |
| 6,699,267 B2 | 3/2004 | Voorhees et al. | |
| 6,749,624 B2 | 6/2004 | Knowlton | |
| D492,773 S | 7/2004 | Ellingboe et al. | |
| 6,764,391 B1 | 7/2004 | Grant et al. | |
| 6,799,063 B2 | 9/2004 | Carson | |
| 6,802,855 B2 | 10/2004 | Ellingboe et al. | |
| 6,818,012 B2 | 11/2004 | Ellingboe | |
| 6,827,728 B2 | 12/2004 | Ellingboe et al. | |
| 6,830,581 B2 | 12/2004 | Magers | |
| 6,921,198 B2 | 7/2005 | Gruszecki et al. | |
| 6,969,399 B2 | 11/2005 | Schock et al. | |
| 7,056,334 B2 | 6/2006 | Lennox | |
| 7,160,259 B2 | 1/2007 | Tardy et al. | |
| 7,640,768 B2 | 1/2010 | Noda et al. | |
| 7,828,831 B1 | 11/2010 | Tanhehco et al. | |
| 8,097,030 B2 | 1/2012 | Stelea et al. | |
| 8,706,207 B2 | 4/2014 | Flint | |
| 9,227,860 B1 * | 1/2016 | King | C02F 1/685 |
| 9,615,983 B2 | 4/2017 | Stryker et al. | |
| 9,776,888 B1 * | 10/2017 | Kurani | C02F 1/008 |
| 2001/0010296 A1 * | 8/2001 | Hirota | C02F 1/46104 |
| | | | 210/175 |
| 2002/0117430 A1 * | 8/2002 | Navarro | C02F 1/008 |
| | | | 210/85 |
| 2004/0165646 A1 | 8/2004 | Shidemantle et al. | |
| 2004/0210283 A1 | 10/2004 | Rose et al. | |
| 2006/0048520 A1 | 3/2006 | Huang et al. | |
| 2006/0235497 A1 | 10/2006 | Zanotti | |
| 2006/0287697 A1 | 12/2006 | Lennox | |
| 2007/0021808 A1 | 1/2007 | Rojas | |
| 2007/0162097 A9 | 7/2007 | Rojas | |
| 2008/0058697 A1 | 3/2008 | Kamen et al. | |
| 2009/0099629 A1 | 4/2009 | Carson et al. | |
| 2009/0240312 A1 | 9/2009 | Koewler | |
| 2010/0139294 A1 | 6/2010 | Lowe et al. | |
| 2010/0193436 A1 * | 8/2010 | Ruehr | B01D 61/025 |
| | | | 210/636 |
| 2011/0152982 A1 | 6/2011 | Richardson | |
| 2011/0238143 A1 * | 9/2011 | Schock | A61F 7/0053 |
| | | | 607/104 |
| 2014/0343639 A1 * | 11/2014 | Hopper | A61F 7/0085 |
| | | | 607/104 |
| 2015/0344323 A1 * | 12/2015 | Mahdjoubi Namin | E03B 1/042 |
| | | | 210/739 |
| 2016/0140307 A1 | 5/2016 | Brosnan et al. | |
| 2017/0348449 A1 | 12/2017 | Ward et al. | |

FOREIGN PATENT DOCUMENTS

| | | |
|---|---|---|
| JP | 5023375 A | 2/1993 |
| WO | 200154635 A1 | 8/2001 |
| WO | 200238091 A1 | 5/2002 |
| WO | 2003030790 A1 | 4/2003 |
| WO | 2004006814 A2 | 1/2004 |
| WO | 2005117546 A2 | 12/2005 |

OTHER PUBLICATIONS

Altrix Precision Temperature Management System Stryker Operations Manuel, Dec. 2016.
Sorin Group, Heater-Cooling System 3T, Operating Instructions (2015).
Specification and Drawings as filed for co-pending U.S. Appl. No. 15/611,048 filed Jun. 1, 2017 entitled Method of Disinfecting a Thermal Control Unit.
Medivance, Arctic Sun 5000, Service Manual, (2010-2011).

* cited by examiner

THERMAL CONTROL SYSTEM

CROSS-REFERENCE TO RELATED APPLICATIONS

This application claims priority to U.S. provisional patent application Ser. No. 62/406,676 filed Oct. 11, 2016, by inventors Marko Kostic et al. and entitled THERMAL CONTROL SYSTEM, the complete disclosure of which is incorporated herein by reference.

BACKGROUND

The present invention relates to a thermal control system for controlling the temperature of circulating fluid which is delivered to one or more thermal pads positioned in contact with a patient.

Thermal control systems are known in the art for controlling the temperature of a patient by supplying temperature-controlled fluid to one or more pads, blankets, or similar structures, that are positioned in contact with, or adjacent to, a patient. The temperature of the fluid is controlled by a thermal control unit that provides fluid to the pads or blankets. After passing through the pads or blankets, the fluid is returned to the control unit where any necessary adjustments to the returning fluid temperature are made before being pumped back to the pad or blanket. In some instances, the temperature of the fluid is controlled to a target fluid temperature, while in other instances the temperature of the fluid is controlled in order to effectuate a target patient temperature. When controlling a patient's temperature, a patient temperature probe may be attached to the control unit in order to provide patient temperature readings as feedback to the control unit so that it can make the necessary temperature adjustments to the circulating fluid.

SUMMARY

The present disclosure provides various improved aspects to a thermal control system. In at least one embodiment, the present disclosure includes a thermal control unit that more effectively ensures that the quality of the circulating fluid meets one or more thresholds. Further, positive indications may be provided to the user both when the fluid meets the cleanliness standards and when the fluid does not meet the cleanliness standards. In some instances, multiple filters are included in the thermal control and used in an economically advantageous manner wherein the more expensive filters are used less frequently than the less expensive filters, thereby reducing the operating costs of the thermal control unit while still ensuring cleanliness standards are maintained. In some instances, the thermal control unit assesses the effectiveness of one or more cleaning actions undertaken to provide feedback to the user regarding the cleaning actions.

According to one embodiment, a thermal control unit for controlling a patient's temperature is provided that includes a fluid outlet, a fluid inlet, a pump, a controller, and a fluid quality monitor. The fluid outlet is adapted to fluidly couple to a fluid supply line, and the fluid inlet is adapted to fluidly couple to a fluid return line. The pump circulates fluid from the fluid inlet through the thermal control unit and to the fluid outlet. The controller controls the temperature of the circulating fluid. The fluid quality monitor monitors a cleanliness of the circulating fluid and issues a signal if the cleanliness of the circulating fluid falls below a threshold.

According to other aspects, the thermal control unit further comprises a user interface adapted to provide a visual indication to a user when the cleanliness of the circulating fluid is above the threshold.

The fluid quality monitor may be adapted to monitor an amount of bacteria in the circulating fluid and/or an amount of disinfectant in the circulating fluid.

In some embodiments, the controller analyzes outputs from the fluid quality monitor and generates a prediction for when the circulating fluid should be cleaned. The prediction may be displayed on the user interface.

In some embodiments, the fluid quality monitor includes a filter through which the circulating fluid flows and a sensor for sensing a characteristic associated with the filter, such as an amount of blockage of the filter. To detect the amount of blockage of the filter, an upstream pressure sensor positioned upstream of the filter and a downstream pressure sensor positioned downstream of the filter are provided in some embodiments. The fluid quality monitor compares an output from the upstream pressure sensor to an output from the downstream pressure sensor. In other embodiments, the amount of blockage is determined by an optical sensor or other type of sensor.

The thermal control unit, in some embodiments, includes a first fluid path and a second fluid path. The first fluid path is arranged in parallel with the second fluid path and the fluid quality monitor is positioned in-line with the second fluid path.

As least twice as much fluid flows through the first fluid path as through the second fluid path, in some embodiments.

The fluid quality monitor, in some embodiments, includes a sensor for detecting biofilm on a surface inside of the thermal control unit that is in contact with the circulating fluid.

According to another aspect of the disclosure, the fluid quality monitor monitors the cleanliness of the fluid by comparing an output from the sensor to a baseline reading.

A dispenser adapted to dispense a cleaning agent in the circulating fluid is included in some embodiments. The controller controls the dispenser based upon an output of the fluid quality monitor.

According to another embodiment, a thermal control unit for controlling a patient's temperature is provided that includes a fluid outlet, a fluid inlet, a heat exchanger, a pump, a valve, and a controller. The fluid outlet is adapted to fluidly couple to a fluid supply line, and the fluid inlet is adapted to fluidly couple to a fluid return line. The pump circulates fluid from the fluid inlet through the heat exchanger and to the fluid outlet. The controller controls the heat exchanger such that a temperature of the circulating fluid is adjusted toward a desired temperature. The controller also controls the valve based upon a measurement of a cleanliness of the circulating fluid.

In an alternative embodiment, the controller is adapted to control the valve based upon the passage of a predetermined amount of time. In still other embodiments, the controller is adapted to control the valve based upon both the cleanliness of the circulating fluid and the passage of predetermined amounts of time.

The valve, in some embodiments, allows a portion of the circulating fluid to flow into an auxiliary path when the valve is open and prevents all of the circulating fluid from flowing into the auxiliary path when the valve is closed. A filter is positioned in the auxiliary path adapted to filter the circulating fluid. In some embodiments, a second filter is positioned outside of the auxiliary path and adapted to filter the circulating fluid. The second filter may have a larger pore size than the filter positioned in the auxiliary path.

The measurement of the cleanliness, in some embodiments, is based upon a measurement made with respect to the second filter.

The controller automatically adds a cleaning agent to the circulating fluid based upon the measurement made with respect to the filter and/or the second filter.

According to another embodiment, a thermal control unit for controlling a patient's temperature is provided that includes a fluid outlet, a fluid inlet, a heat exchanger, a pump, a first filter, a valve, a second filter, and a controller. The fluid outlet is adapted to fluidly couple to a fluid supply line, and the fluid inlet is adapted to fluidly couple to a fluid return line. The pump circulates fluid along a primary fluid path from the fluid inlet through the heat exchanger and to the fluid outlet. The first filter is positioned in the primary fluid path and adapted to filter fluid flowing through the primary fluid path. The second filter is positioned along an auxiliary path. The controller controls the heat exchanger such that a temperature of the circulating fluid is adjusted toward a desired temperature. The controller also controls the valve such that fluid flows through the auxiliary path only in response to a specific event.

In various embodiments, the specific event includes one or more of the following: a passage of a predetermined amount of time; the taking of a measurement along the primary fluid path of the cleanliness of the circulating fluid; the usage of the thermal control unit with a new patient; and/or the manual activation of a control on the user interface of the thermal control unit.

In some embodiments, the second filter is part of a fluid quality monitor adapted to monitor a cleanliness of the circulating fluid. The controller analyzes outputs from the fluid quality monitor and, in some embodiments, generates a prediction for when the circulating fluid should be cleaned.

The second filter has a smaller pore size than the first filter, in some embodiments.

A second valve may also be included that selectively diverts the circulating fluid toward a second auxiliary path. In some such embodiments, a third filter is positioned along the second auxiliary path.

The third filter may have a pore size smaller than the second filter. In some embodiments, the third filter has a pore size adapted to filter out particles having a size larger than 0.2 microns.

The controller opens the second valve, in some embodiments, so as to allow fluid to flow through the second auxiliary path in response to a cleaning action taken with respect to the circulating fluid. The cleaning action may be the dispensing of a disinfectant into the circulating fluid, the replacement of the circulating fluid with fresh circulating fluid, and/or the application of ultraviolet light to the circulating fluid.

In some embodiments, the second auxiliary path is defined such that fluid flowing through the third filter must first flow through the second filter in order to reach the third filter.

The controller may use a measurement associated with the third filter to determine if the cleaning action was effective or not.

In some embodiments, the controller closes the second valve after a measurement of the effectiveness of a cleaning action has been taken along the second auxiliary path.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
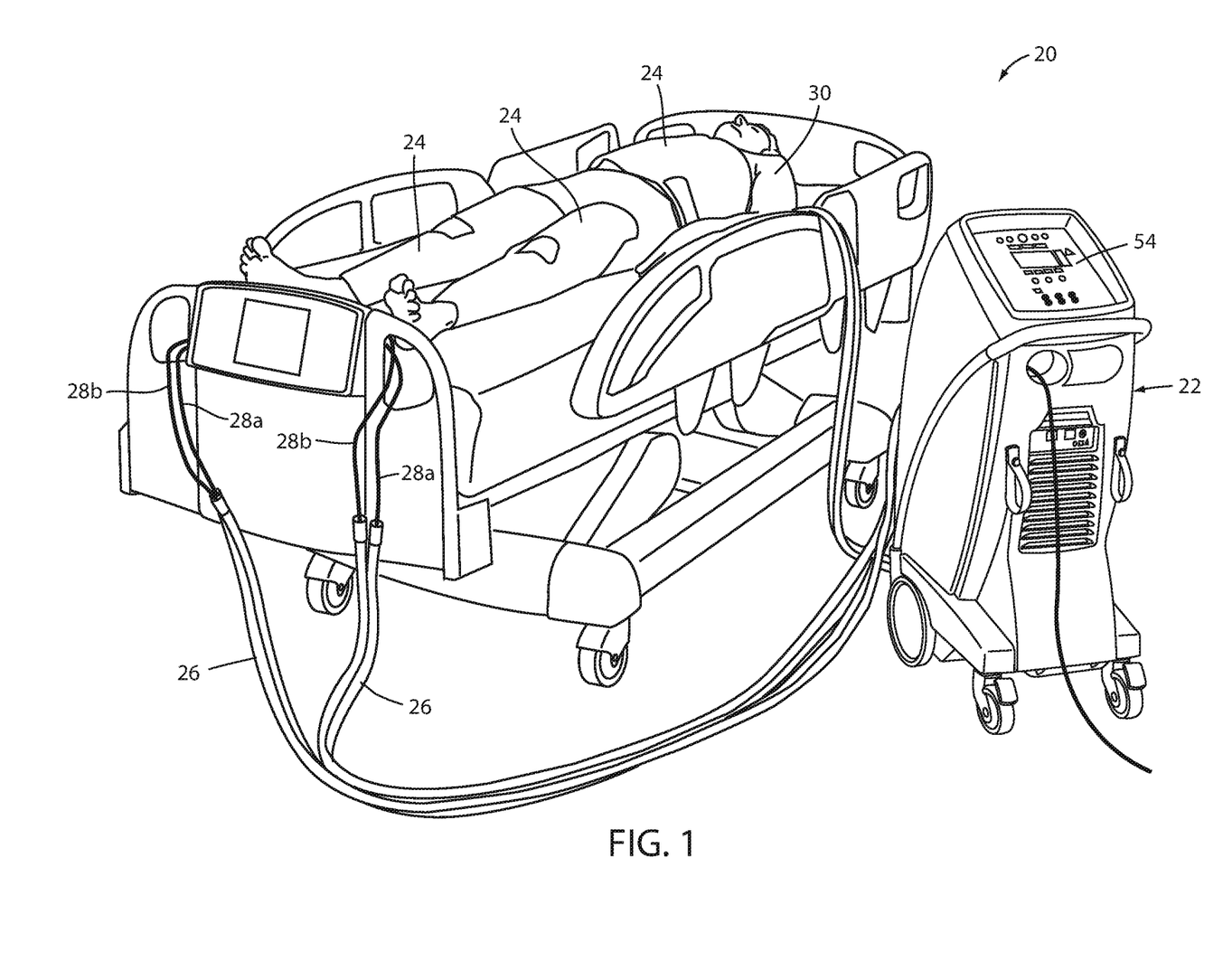
FIG. 1 is a perspective view of a thermal control system that may be used to provide thermal treatment to a patient.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each hose includes one or more lines 28. In the embodiment shown in FIG. 1, each hose 26 includes a fluid supply line 28a and a fluid return line 28b. In alternative embodiments, hoses 26 may include additional fluid supply lines 28a and return lines 28b and/or one or more control lines, such as disclosed in commonly assigned U.S. patent application Ser. No. 62/373,565 filed Aug. 11, 2016, by inventor James Galer and entitled THERMAL SYSTEM, the complete disclosure of which is hereby incorporated herein by reference. In still other alternative embodiments, hoses 26 may also or alternatively include one or more auxiliary lines that function in the manner disclosed in commonly assigned U.S. patent application Ser. No. 62/373,658 filed Aug. 11, 2016, by inventors James Galer et al. and entitled THERMAL THERAPY DEVICES, the complete disclosure of which is also incorporated herein by reference. In still other embodiments, hoses 26 may be constructed to include only a single fluid line (supply or return). Still other constructions are possible.

Thermal control unit 22 delivers temperature controlled fluid (such as, but not limited to, water) to the thermal pads 24 via the fluid supply lines 28a. After the temperature controlled fluid has passed through thermal pads 24, thermal control unit 22 receives the temperature controlled fluid back from thermal pads 24 via the return lines 28b.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply lines 28a, the temperature of the patient 30 can be controlled via the close contact of the pads 24 with the patient 30 and the resultant heat transfer therebetween.

Figure 2:
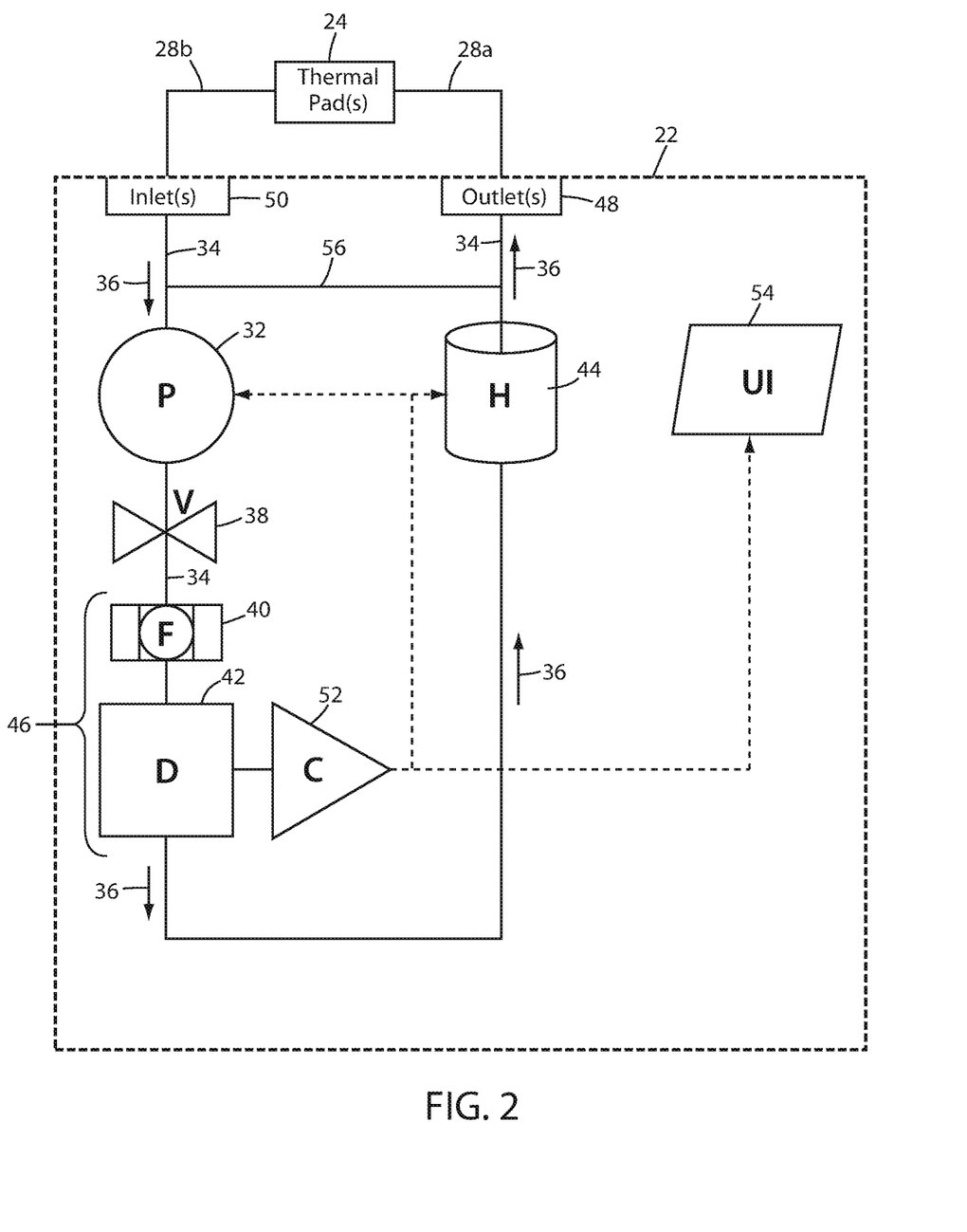
FIG. 2 is a block diagram of a first embodiment of the thermal control unit of FIG. 1.

Thermal control unit 22 is adapted to raise or lower the temperature of the fluid supplied to thermal pads 24 via supply lines 28a. As shown in FIG. 2, thermal control unit 22 includes a pump 32 for circulating fluid through a primary fluid path 34. Pump 32, when activated, circulates the fluid through primary fluid path 34 in the direction of arrows 36 (counterclockwise in FIG. 2). Starting at pump 32 the circulating fluid passes through a valve 38, a filter 40, a detector 42, and a heat exchanger 44. As will be described in more detail below, filter 40 and detector 42 define a fluid quality monitor 46. After passing through heat exchanger 44, the circulating fluid is delivered to one or more fluid outlets 48. Fluid outlets 48 are adapted to couple to one or more fluid supply lines 28a that deliver temperature controlled fluid to one or more thermal pads 24. After the temperature controlled fluid has flowed through the thermal pads 24, it returns to thermal control unit 22 via one or more return lines 28b. The return lines 28b are coupled to one or more fluid inlets 50 on thermal control unit 22. Fluid inlets 50 are in fluid communication with primary fluid path 34 and direct the fluid returning from pads 24 to pump 32. Pump 32 pumps the returning fluid in the manner previously described and the fluid thereby circulates between thermal control unit 22 and the one or more thermal pads 24.

A controller 52 is also provided within thermal control unit 22. Controller 52 is adapted to control heat exchanger 44, pump 32, and valve 38. Controller 52 is also in communication with one or more temperature sensors (not shown) that sense the temperature of the circulating fluid. Controller 52 uses the outputs from the temperature sensor(s) to adjust heat exchanger 44 so that the fluid delivered to the thermal pad(s) 24 is at a desired temperature. In some embodiments, controller 52 uses the outputs from the one or more temperature sensors to effectuate closed-loop control of the temperature of the circulating fluid.

Controller 52 is also in communication with a user interface 54, which may be a control panel or other type of user interface. User interface 54 includes controls enabling a user to turn control unit 22 on and off, as well as one or more controls enabling the user to select a target temperature for the fluid delivered to thermal pads 24. In some embodiments, user interface 54 also allows a user to select a target temperature for the patient being treated, rather than a specific target temperature for the fluid. When this feature is present, controller 52 makes automatic adjustments to the temperature of the fluid in order to bring the patient's temperature to the desired patient target temperature. In addition, user interface 54 allows a user to configure how thermal control unit 22 controls the thermal pads in light of temperature and/or flow information received by thermal control unit 22.

Control unit 22 also includes a bypass line 56 fluidly coupled to primary fluid path 34 near the outlet(s) 48 and inlet(s) 50. Bypass line 56 allows fluid to circulate through primary fluid path 34 even in the absence of any thermal pads 24 or lines 28a being coupled to any of outlets 48. This allows thermal control unit 22 to circulate the fluid internally and adjust the temperature of the fluid prior to any thermal pad(s) 24 being coupled to thermal control unit 22.

Although not illustrated in FIG. 2, thermal control unit 22 includes either a reservoir or a tank for storing the fluid. When a reservoir is included, the reservoir may be coupled to primary fluid path 34 so as to deliver fluid to path 34, yet not positioned in-line with primary fluid path 34. That is, the reservoir is positioned such that fluid is able to circulate within thermal control unit 22 without passing through the reservoir. In this manner, any fluid that remains in the reservoir does not need to have its temperature adjusted, and thermal control unit 22 therefore does not need to expend any energy changing the temperature of the fluid that remains inside the reservoir. In those embodiments of thermal control unit 22 that include such a reservoir, the reservoir may be constructed in any of the manners disclosed in commonly assigned U.S. patent application Ser. No. 14/282,383 filed May 20, 2014, by inventors Christopher Hopper et al. and entitled THERMAL CONTROL SYSTEM, the complete disclosure of which is hereby incorporated herein by reference. Other constructions of the reservoir may also be used. Still further, in some embodiments, a tank is used to store the fluid and the tank is positioned in-line with primary fluid path 34 such that fluid flowing on fluid path 34 must flow through the tank. The flowing fluid mixes with any fluid inside the tank before being pumped out of tank and further along primary fluid path 34.

Although also not illustrated in FIG. 2, thermal control unit 22 also includes, in some embodiments, an air separator that removes air from the primary fluid path 34, hoses 26, and thermal pads 24. In some embodiments, the air separator is constructed in any of the manners disclosed in commonly assigned U.S. patent application Ser. No. 62/361,124 filed Jul. 12, 2016, by inventor Gregory S. Taylor and entitled THERMAL CONTROL SYSTEM, the complete disclosure of which is hereby incorporated herein by reference. In alternative embodiments, the air separator may be constructed in different manners, or omitted altogether.

Controller 52 includes any and all electrical circuitry and components necessary to carry out the functions and algorithms described herein, as would be known to one of ordinary skill in the art. Generally speaking, controller 52 may include one or more microcontrollers, microprocessors, and/or other programmable electronics that are programmed to carry out the functions described herein. It will be understood that controller 52 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/ or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

Controller 52 uses the outputs of one or more temperature sensors to control heat exchanger 44 and/or pump 32. Controller 52 controls the heat exchanger and/or pump 32 such that the temperature of the circulating fluid has its temperature adjusted (or maintained) in accordance with the operating mode (manual or automatic) selected by the user of thermal control unit 22. Controller 52 may control the temperature of the fluid using a closed-loop proportional-integral (PI) controller, a closed-loop proportional-integral-derivative (PID), controller, or some other type of closed-loop controller.

Control unit 22 may also be modified to include one or more flow sensors that measure the rate of fluid flow and report this information to controller 52. In such modified embodiments, controller 52 uses the flow rate in determining what control signals to send to heat exchanger 44, valve 38, and pump 32.

It will be understood by those skilled in the art that the particular order of the components along primary fluid path 34 of control unit 22 may be varied from what is shown in FIG. 2. For example, although FIG. 2 depicts pump 32 as being upstream of heat exchanger 44 and several other components, this order may be changed. Pump 32, fluid quality monitor 46, heat exchanger 44, and valve 62 may be positioned at any suitable location along primary fluid path 34 and in any suitable order.

Further details regarding the construction and operation of one embodiment of thermal control unit 22 that are not described herein are found in commonly assigned U.S. patent application Ser. No. 14/282,383 filed May 20, 2014, by inventors Christopher Hopper et al. and entitled THERMAL CONTROL SYSTEM, the complete disclosure of which has been incorporated herein by reference.

Fluid quality monitor 46 of FIG. 2, as noted, includes filter 40 and detector 42. Filter 40 is adapted to filter out particles within the circulating fluid, such as, but not limited to, biological materials. As filter 40 filters these particles out of the circulating fluid, the pores within filter 40 tend to become more and more plugged with the filtered particles.

Detector 42 is adapted to detect how plugged filter 40 has become and to provide an indication to the user when filter 40 is in need of replacement. In some embodiments, controller 52 keeps track of the rate at which filter 40 is accumulating more and more particles and generates, based on extrapolation of the rate, an estimated time in the future that filter 40 will need replacement. Controller 52 outputs this estimated replacement date to user interface 54, which displays it to the user, thereby providing the user with advance notification of an upcoming need to replace filter 40.

In some embodiments, detector 42 determines the degree to which filter 40 has become blocked by contaminants by measuring a pressure difference across filter 40 and comparing it to a baseline pressure difference or another type of threshold. When comparing to a baseline pressure difference, detector 42 measures a fluid pressure difference across filter 40 when filter 40 is initially installed (or a relatively short time thereafter). This pressure drop is recorded in memory and used as a baseline reading against which future pressure drop measurements are compared. In some embodiments, pump 32 is operated at only two levels: off and on. In such embodiments, controller 52 instructs detector 42 to take a baseline reading when pump 32 is on. In other embodiments, controller 52 controls pump 32 at a plurality of different non-zero speeds. In these latter embodiments, controller 52 is configured to instruct detector 42 to take a plurality of different baseline readings of the pressure drop across filter 40 at different pump levels. When future pressure drop readings are taken, controller 52 records the level at which pump 32 is being driven when those future drop readings are taken and compares those pressure drop readings to a baseline pressure drop reading that was taken when pump 32 was operated at the same level. This method therefore adjusts for differing pressure drops across filter 40 that are due to pump 32 being operated at different levels, rather than being due to different levels of obstruction of filter 40.

In an alternative embodiment, detector 42 comprises an optical detector. The optical detector, in some embodiments, emits an optical signal onto filter 40 and measures an amount of the optical signal that is transmitted through filter 40 and/or reflected back from filter 40. The amplitude of the signal that is transmitted through filter 40 decreases as the filter 40 becomes more and more obstructed by filtered particles. Conversely, the amplitude the optical signal that is reflected back from filter 40 tends to increase as the filter 40 becomes more and more obstructed by filtered particles. Using either or both of these measurements (transmittance and/or reflectance) therefore enables detector 42 to determine the degree to which filter 40 has become obstructed. Controller 52 uses this information to determine when or how soon filter 40 should be replaced.

In alternative embodiments, detector 42 comprises an optical detector that takes optical readings of the circulating fluid. That is, rather than, or in addition to, emitting light onto filter 40, the optical detector emits light that passes through the circulating fluid. The amount of scattering and/or reflectance is measured and recorded and used for assessing the quality of the circulating fluid. Such optical readings may also be taken with respect to interior surfaces of the primary fluid path 34 to determine if, and how much of, any biofilm growth has occurred on such surfaces.

When using the readings from detector 42 to determine when filter 40 should be replaced, controller 52 compares the optical readings to one or more baseline readings taken when filter 40 was not obstructed (and/or when the circulating fluid was known to be clean and/or when biofilm was known to be absent), in at least some embodiments. In some of these embodiments, the baseline readings are taken by the manufacturer and stored in a memory accessible to controller 52. In other embodiments, the baseline readings are taken at one or more times after the customer has purchased the thermal control unit 22. In some of these embodiments, controller 52 is programmed to take a baseline reading, or multiple baseline readings, after filter 40 has been changed and a new filter 40 is present. In such embodiments, thermal control unit 22 may include a sensor for detecting the presence of a new filter 40, and/or a user may instruct controller 52 via user interface 54 that a new filter 40 has been installed. Shortly thereafter, controller 52 takes one or more baseline readings of the amount of obstruction of filter 40 (by either measuring the pressure difference associated with filter 40 or the optical characteristics of filter 40). The baseline readings are stored in memory and used for comparison purposes against future readings.

In some embodiments, controller 52 determines whether a new filter 40 is needed and/or whether the circulating fluid is clean or not based upon whether or not such subsequent readings differ from the baseline reading by a predetermined threshold. In other embodiments, multiple thresholds are used—one for indicating that a new filter should be installed in X amount of time, another for indicating that a new filter 40 should be installed in Y amount of time, and perhaps even more thresholds for even different amounts of time. Thus, if controller 52 determines from a current readings associated with filter 40 that it differs from the baseline reading by, for example, 40%, controller 52 may indicate on user interface 54 that the filter 40 should be changed within the next week, several weeks, or months. If controller 52 determines that the current readings associated with filter 40 differ from the baseline reading by, for example, 80%, controller 52 may indicate on user interface 54 that the filter 40 should be changed immediately, or within some other shortened time period. In still other embodiments, controller 52 is adapted to provide indications of when filter 40 should be changed that are based, not on time, but on a number of uses, or some other quantity. Thus, for example, instead of recommending that filter 40 be changed in a week, user interface 54 may display a message instructing the user to change filter 40 after three more uses of thermal control unit 22, or the next time thermal control unit 22 is used, or some other number of uses.

In addition to, or as an alternative to, providing indications to the user of when filter 40 should be replaced, controller 52 is further adapted to use fluid quality monitor 46 to provide fluid quality information to the user of thermal control unit 22. In some such embodiments, controller 52 provides instructions to the user recommending when he or she should change the circulating fluid used with thermal control unit 22 and/or clean thermal control unit 22. Controller 52 generates this information by using the aforementioned pressure and/or optical measurements of filter 40 (carried out by detector 42). Controller 52, however, uses different baseline readings when providing feedback information to the user about the quality of the fluid and/or the need for cleaning of thermal control unit 22.

In some embodiments, thermal control unit 22 instructs fluid quality monitor 46 to take one or more baseline readings (of the filter obstruction, of the fluid's optical properties, and/or of the biofilm levels) whenever the circulating fluid has been changed and/or whenever thermal control unit 22 has been cleaned. Controller 52 then uses those baselines readings for comparing against future readings taken with respect to filter 40. These comparisons may be different from the comparisons used by controller 52 when determining whether or not filter 40 should be replaced. As one example, in some embodiments, controller 52 is programmed to recommend that the circulating fluid is replaced and/or thermal control unit 22 is cleaned every time the obstruction of filter 40 increases by a threshold amount (or percentage) in comparison to the baseline readings taken when the fluid was last changed and/or the thermal control unit 22 was last cleaned. Thus, in some of these embodiments, thermal control unit 22 provides notification to the user of both when filter 40 should be changed and when the circulating fluid should be changed or cleaned (and/or when thermal control unit 22 itself should be cleaned). The cleaning of thermal control unit 22 and the changing of the circulating fluid don't necessarily coincide with the changing of filter 40. That is, the fluid may be desirably changed and/or thermal control unit 22 desirably cleaned more often than filter 40 is replaced, or vice versa.

In the embodiment shown in FIG. 2, controller 52 controls the amount of fluid flowing through filter 40 and heat exchanger 44 by controlling the degree to which valve 38 is opened or closed. In some embodiments, controller 52 controls valve 38 as part of its control over the temperature of the circulating fluid. Thus, in one illustrative example, if the circulating fluid returns to thermal control unit 22 at a temperature significantly different from the temperature delivered to outlet(s) 48, controller 52 may open valve 38 completely so that more fluid flows to heat exchanger 44 for temperature conditioning, and thereby providing more fluid volume to the thermal pads 24. On the other hand, if the temperature of the returning fluid is nearly the same as the temperature of the outgoing fluid delivered to thermal pads 24, controller 52 may be controlled to reduce the fluid flow via valve 38. Valve 38 may also be controlled in other manners. Still further, in some modified embodiments of the thermal control unit 22 of FIG. 2, valve 38 is omitted.

Figure 3:
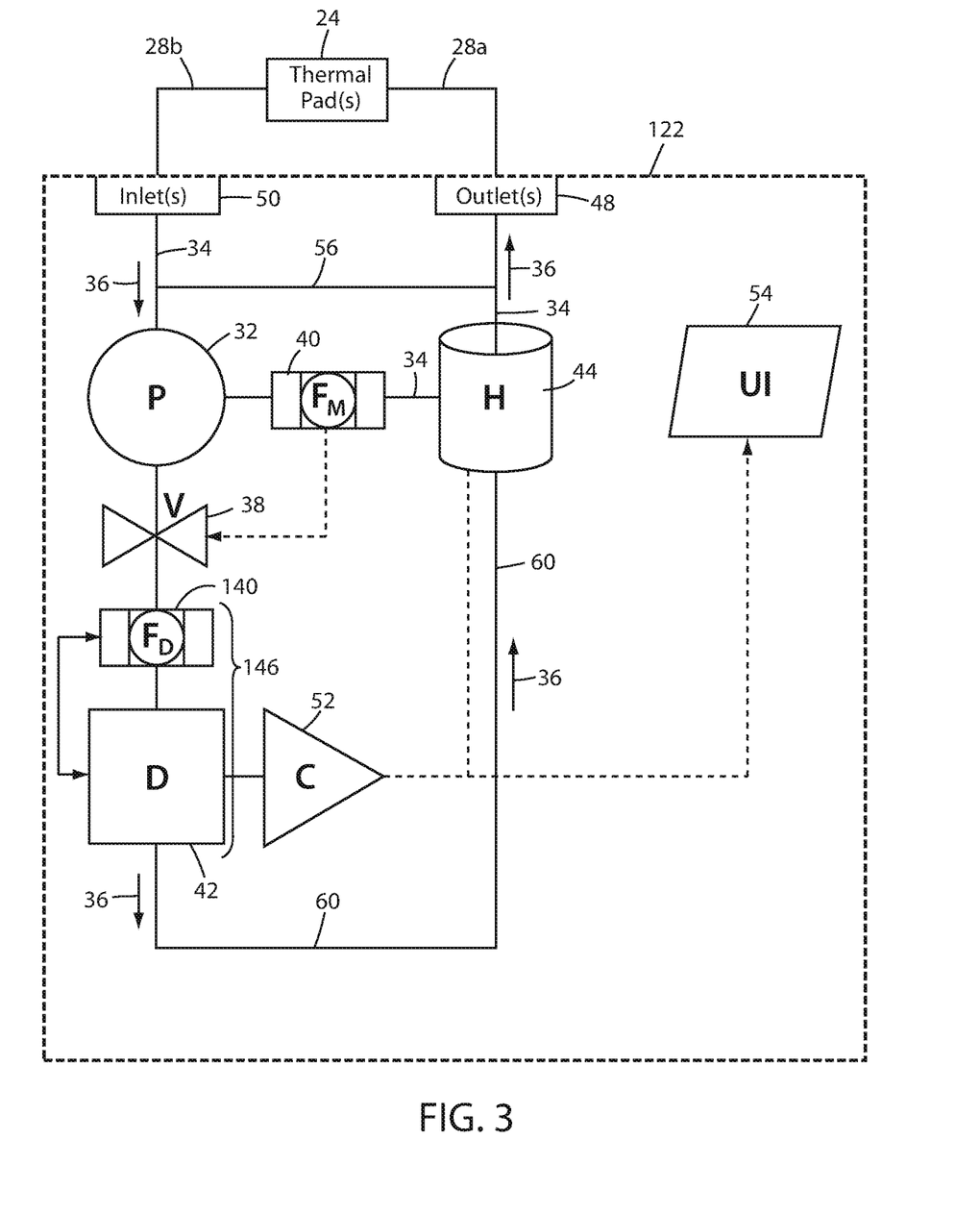
FIG. 3 is a block diagram of a second embodiment of the thermal control unit of FIG. 1.

FIG. 3 illustrates an alternative embodiment of a thermal control unit 122 according to the present disclosure. Thermal control unit 122 includes a number of components and/or features that are the same as thermal control unit 22. Those components or features that are common are labeled with the same reference numbers used to describe thermal control unit 22 and, unless otherwise explicitly stated below, operate in the same manner or provide the same function as previously described. Those components or features that are different from thermal control unit 22 are provided with a new reference number and described in more detail below.

Thermal control unit 122 differs from thermal control unit 22 primarily in that thermal control unit 122 includes a second filter 140 and an auxiliary fluid path 60. During operation of thermal control unit 22, the circulating fluid primarily flows along primary fluid path 34. That is, valve 38 is closed more often than not so that fluid returning from thermal pads 24 does not enter auxiliary path 60, but instead flows through filter 40 and heat exchanger 44 (after passing through pump 32). Intermittently, controller 52 opens valve 38 to allow a portion of the fluid flowing in primary fluid path 34 to enter into auxiliary fluid path 60. Controller 52 does this to check on the quality (e.g. cleanliness) of the fluid flowing within thermal control unit 122.

In some embodiments, controller 52 opens valve 38 periodically based upon the passage of predetermined amounts of time. In such embodiments, the predetermined amounts of time may be based upon the passage of absolute amounts of time, or relative amounts of time (such as, but not limited to, the amount of time that passes during which thermal control unit 122 is turned on, or pumping fluid to a thermal pad 24). Whenever pump 32 is activated, the circulating fluid passes through filter 40 and is filtered. Filter 40 is designed to remove contaminants from the circulating fluid. Filter 40 therefore helps ensure that the circulating fluid is clean. However, filter 40, in some embodiments, is not designed to remove all biological materials from the circulating fluid. In such embodiments, filter 40 may be a filter having a pore size that is greater than 0.2 microns. Because of this size, bacteria, mycobacteria, and/or other biological organisms—which may be as small as approximately 0.2 microns—may not be completely removed from the circulating fluid via filter 40.

Second filter 140, however, is, in some embodiments, constructed to have a smaller pore size than filter 40, and thereby able to remove smaller contaminants. Indeed, in some embodiments, second filter 140 may have a pore size that is adapted to remove all biological organisms, including bacteria and mycobacteria from the circulating fluid. In other embodiments, second filter 140 may not remove all organisms, but still filter outs smaller contaminants than filter 40.

Controller 52 uses second filter 140, in some embodiments, to provide a positive indication to the user of thermal control unit 122 that the circulating fluid is clean. In such embodiments, controller 52 uses detector 42 to measure one or more characteristics of filter 140 when valve 38 is opened in the same manner discussed above with respect to filter 40 and detector 42 of thermal control unit 22. That is, detector 42 of thermal control unit 22 measures the pressure difference and/or one or more optical characteristics of second filter 140 (and/or the circulating fluid) when fluid is flowing along auxiliary path 60. Based on these measurements, controller 52 determines whether the fluid is sufficiently clean or not and reports the results of this determination to user interface 54. After taking a suitable number of measurements, controller 52 closes valve 38, cutting off fluid flow to auxiliary path 60, and stops taking measurements using detector 42.

In some embodiments, controller 52 opens valve 38 and takes fluid quality measurements with fluid quality monitor 146 (e.g. filter 140 and detector 42) whenever one or more predetermined events occur. For example, whenever a user replaces the fluid inside of thermal control unit 122, replaces filter 40 and/or 140, cleans thermal control unit 122, initially turns on power to thermal control unit 122, uses thermal control unit 122 with a new patient, and/or in response to other events, controller 52 opens valve 38 and uses fluid quality monitor 146 to assess the quality of the circulating fluid. If the assessment criteria are met, controller 52 provides positive confirmation to the user that the circulating fluid meets one or more predetermined cleanliness standards. If the assessment criteria are not met, controller 52 provides a positive indication to the user that thermal control unit 122 should be cleaned and/or its fluid replaced.

Thermal control unit 122, in at least some embodiments, provides positive feedback to a user about the quality of the cleaning job performed on thermal control unit 122. In such embodiments, after thermal control unit 122 has been cleaned and/or disinfected, controller 52 opens valve 38 and allows fluid to flow through fluid quality monitor 146. Monitor 146 detects one or more characteristics of filter 140 (e.g. pressure difference, optical characteristics, etc.) and/or of the circulating fluid to determine whether the cleaning was successful or not. In detecting these characteristics, monitor 146 may be configured to take new readings every time monitor 146 takes measurements and to compare those to the previous measurements. When so doing, controller 52 looks for the amount of additional particulate matter that has been recently trapped in filter 140 as compared to the amount that was previously trapped therein. Alternatively, controller 52 compares the amount of particulate matter circulating in the fluid to one or more previously defined baselines or thresholds. These differences are indications of whether or not thermal control unit 122 has been sufficiently cleaned or not. Controller 52 outputs a message to user interface 54 indicating whether or not the fluid is clean or not.

Because second filter 140 is only used periodically during the operation of thermal control unit 122, it will tend to need replacement less frequently than filter 40. Filter 140 may therefore advantageously be implemented as a more expensive and smaller pore-size filter than filter 40. Indeed, in some embodiments, filter 140 has a pore size small enough to remove contaminants of 0.2 microns or greater.

Figure 4:
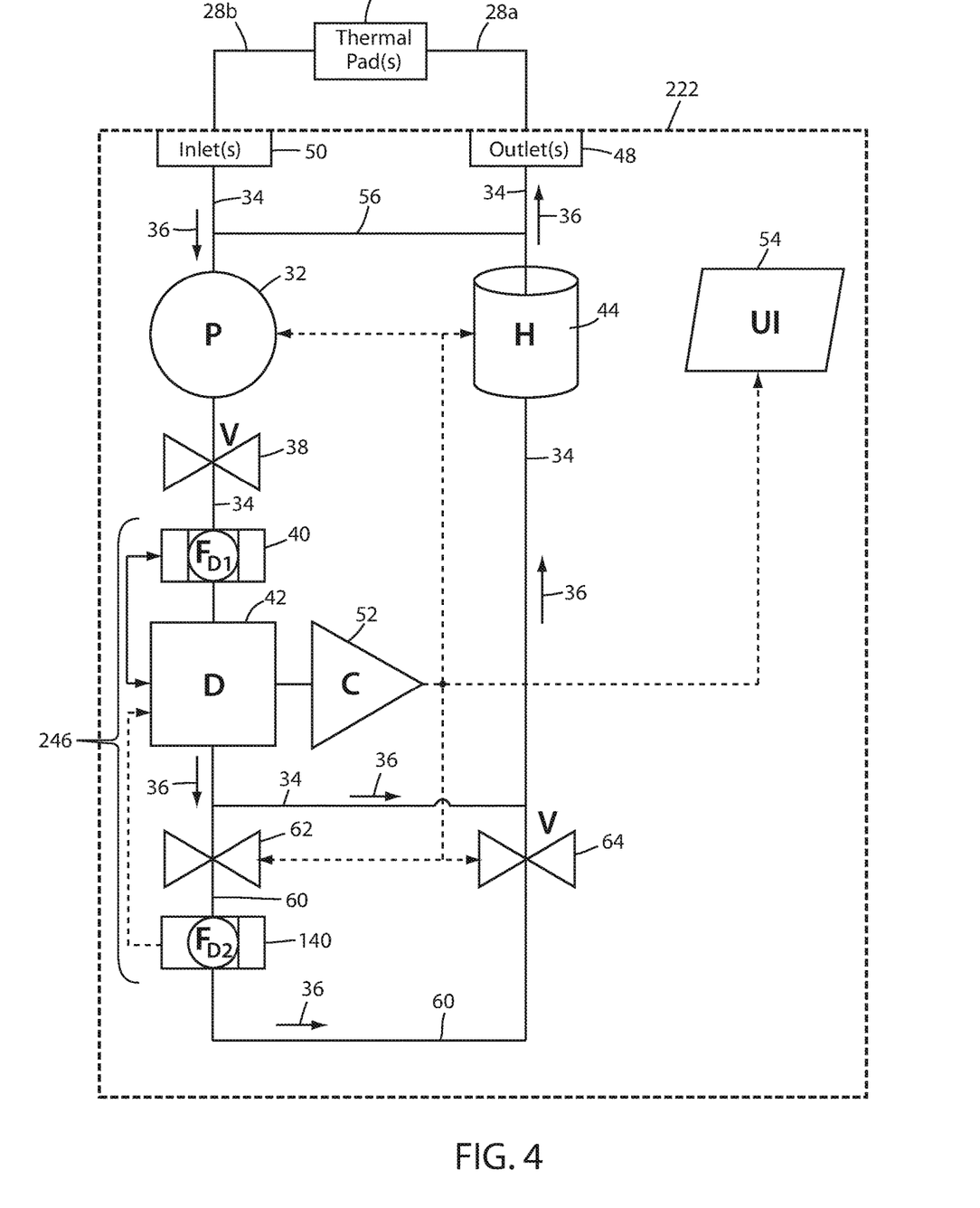
FIG. 4 is a block diagram of a third embodiment of the thermal control unit of FIG. 1.

FIG. 4 illustrates another alternative embodiment of a thermal control unit 222 according to the present disclosure. Thermal control unit 222 includes a number of components and/or features that are the same as thermal control unit 22 and/or 122. Those components or features that are common are labeled with the same reference numbers used to describe thermal control unit 22 and/or 122 and, unless otherwise explicitly stated below, operate in the same manner or provide the same function as previously described. Those components or features that are different from thermal control unit 22 and/or 122 are provided with a new reference number and described in more detail below.

Thermal control unit 222 differs from thermal control unit 122 primarily in that thermal control unit 222 has detector 42 coupled to two filters: filter 40 of primary fluid path 34 and second filter 140 of auxiliary fluid path 60. Detector 42 repetitively takes readings of filter 40 during the operation of thermal control unit 222. If the readings detect more than an acceptable amount of particulates in the circulating fluid, controller 52 notifies the user. In some embodiments, controller 52 also automatically takes steps to clean the circulating fluid. In other embodiments, controller 52 waits for instructions from the user (received via user interface 54) to clean the fluid.

In order to clean the circulating fluid, controller 52 opens valves 62 and 64, thereby allowing fluid from primary fluid path 34 to flow through auxiliary fluid path 60 and return back to primary fluid path 34. When the fluid flows along auxiliary path 60, the fluid passes through second filter 140. Second filter 140 has a smaller pore size than filter 40, and is therefore able to clean the circulating fluid of more particulates than filter 40. By allowing fluid to flow through second filter 140 for a sufficient amount of time, the circulating fluid can be cleaned of substantially all particulates having a size greater than the pore size of second filter 140. After the cleaning is completed, valves 62 and 64 are closed, thereby cutting off fluid flow through second filter 140. Second filter 140 is therefore only occasionally used while first filter 40 is always in use.

Detector 42 operates in conjunction with both filters 40 and 140 to detect the amount of obstruction of these filters and to issue notifications to the user if either one of them becomes obstructed by more than one or more thresholds. As discussed previously, the varying thresholds may be used to provide indications of how soon either or both of the filters 40, 140 should be changed. Further, as previously noted, detector 42 may be used to monitor filter 40 and determine when valves 62 and 64 should be opened so that cleaning may be performed by second filter 140.

Controller 52 is also, or alternatively, programmed in some embodiments of thermal control unit 222 to control valves 62 and 64 for use in verifying the cleaning efficacy of the user. That is, in some embodiments, controller 52 opens valves 62 and 64 after thermal control unit 222 has been cleaned and/or after the fluid used in thermal control unit 222 has been replaced. After either or both of such actions, controller 52 opens valves 62 and 64 in order to take measurements with respect to second filter 140 to confirm that the cleaning actions undertaken by the user have resulted in clean fluid, as measured by the more stringent standards of second filter 140 (as compared to first filter 40). If controller 52 detects via second filter 140 that more than an acceptable amount of particulates are present in the circulating fluid, it sends a message to user interface 54 instructing it to notify the user that the cleaning efforts were not satisfactory. On the other hand, if no more than an acceptable amount of particulates are present in the circulating fluid, it sends a message to user interface 54 instructing it to notify the user that the cleaning efforts were successful. In some embodiments, controller 52 is also programmed to perform such testing of the circulating fluid in response to a user manually requesting it via user interface 54 (in addition to, or in lieu of, the automatic testing performed after the fluid is changed and/or thermal control unit 222 is cleaned).

Figure 5:
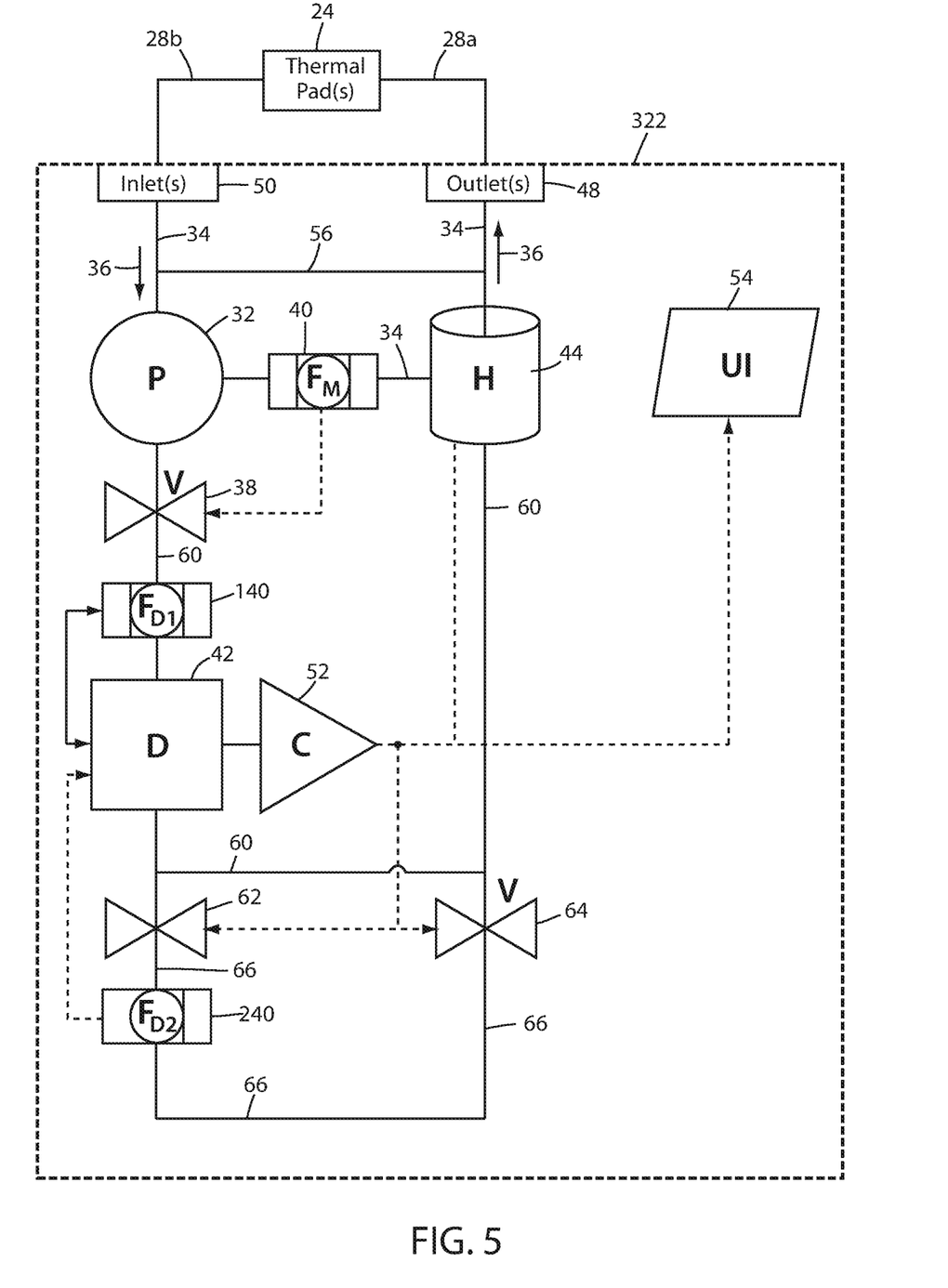
FIG. 5 is a block diagram of a fourth embodiment of the thermal control unit of FIG. 1.

FIG. 5 illustrates yet another alternative embodiment of a thermal control unit 322 according to the present disclosure. Thermal control unit 322 includes a number of components and/or features that are the same as thermal control unit 22, 122, and/or 222. Those components or features that are common are labeled with the same reference numbers used to describe thermal control unit 22, 122, and/or 222 and, unless otherwise explicitly stated below, operate in the same manner or provide the same function as previously described. Those components or features that are different from thermal control unit 22, 122, and/or 222 are provided with a new reference number and described in more detail below.

Thermal control unit 322 includes a primary fluid path 34 and an auxiliary fluid path 60 that are substantially the same as the primary fluid path 34 and auxiliary fluid path 60 of thermal control unit 122 (FIG. 3). Thermal control unit 322, however, differs from thermal control unit 122 in that it includes a second auxiliary fluid path 66. Fluid flow through second auxiliary fluid path 66 is controlled by the opening and closing of valves 62 and 64, which are operated under the control of controller 52. Controller 52 controls the valves 62 and 64, in some embodiments, in the same manner as controller 52 of thermal control unit 222 controls valves 62 and 64. That is, in some embodiments, controller 52 diverts fluid through second auxiliary path 66 for either or both of the following purposes: (1) to clean the circulating fluid, and (2) to check the efficacy of a user-undertaken cleaning effort (e.g. changing the fluid, adding disinfectant to the fluid, cleaning thermal control unit 322 in another manner, etc.).

Controller 52 opens valve 38, which allows fluid to flow from primary fluid path 34 to auxiliary fluid path 60, for any of the same reasons discussed above that controller 52 of thermal control unit 122 opens valve 38. That is, controller 52 of thermal control unit 322 opens valve 38, in at least some embodiments, whenever a user replaces the fluid inside of thermal control unit 322, replaces filter 40, 140, and/or 240, cleans thermal control unit 322, initially turns on power to thermal control unit 322, uses thermal control unit 322 with a new patient, and/or in response to other events. After opening valve 38 and taking one or more measurements of second filter 140 via detector 42, controller 52 analyzes the results to determine whether or not to also open valves 62 and 64 or not.

In some embodiments, controller 52 allows fluid to flow through second filter 140 for a predetermined amount of time, or after a predetermined amount of fluid has passed therethrough. This allows second filter 140 to substantially filter out all of the particles in the circulating fluid that are larger than the pore size of second fluid 140. After this time period has passed, controller 52 opens valves 62 and 64 to allow fluid from auxiliary path 60 to flow to second auxiliary path 66. As shown in FIG. 5, second auxiliary path 66 includes third filter 240. Third filter 240, in some embodiments, includes a smaller pore size than second filter 140 (and second filter 140 includes a smaller pore size than first filter 40). By allowing the circulating fluid to first flow through second filter 140 and remove most, if not all, of the particles that are larger than the pore size of second filter 140, the longevity of third filter 240 can be extended. Thus, third filter 240 may be a relatively more expensive filter that is only subjected to circulating fluid that has been, in effect, prefiltered by filters 40 and 140. Third filter 240 should therefore be able to effectively operate for a relatively long period of time before needing replacement.

In some embodiments, after controller 52 has opened valve 38 and allowed fluid to flow through auxiliary path 60 (but not second auxiliary path 66), controller 52 may not open up second auxiliary path 66 to fluid flow if detector 42 detects too many contaminants are in the fluid via its measurements made with respect to second filter 140. In such cases, controller 52 notifies the user that the circulating fluid is not sufficiently clean. Controller 52 may then close valve 38, shutting off fluid flow to auxiliary fluid path 60. Alternatively, controller 52 may allow valve 38 to remain open so that the circulating fluid is filtered by second filter 140.

It will be understood by those skilled in the art that, although detector 42 has primarily been described with respect to thermal control units 122, 222, and 322 as performing fluid quality measurements, detector 42 may also or alternatively be used in any of these embodiments (as well as thermal control unit 22) to detect when its associated filter(s) should be replaced. Thus, detector 42 is used in some embodiments of thermal control units 122, 222, and 322 to assess the quality of the circulating fluid only, and in other embodiments of thermal control units 122, 222, and 322 to assess both the quality of the circulating fluid and the need for any filter replacements.

It will also be understood by those skilled in the art that although fluid quality monitors 46, 146, and 246 have primarily been described herein as performing fluid quality measurements based upon optical or pressure characteristics of an associated filter, fluid quality monitors 46, 146, and/or 246 may be modified to assess the quality of the circulating fluid in different manners. For example, fluid quality monitors 46, 146, and/or 246 may alternatively or additionally use any of the following techniques for assessing the quality of the circulating fluid: (1) measure a pH (acidity or basicity) level of the circulating fluid; (2) measure the electrical conductivity of the circulating fluid; (3) measure amounts of a disinfectant in the circulating fluid (e.g. chlorine, hydrogen peroxide, ozone, chlorine dioxide, sodium dichloroisocyanurate (NaDCC), etc.); (4) measure amounts of oxygen and/or carbon dioxide in the circulating fluid; (5) measure amounts of ATP (adenosine triphosphate) in the circulating fluid using a luminometer and/or other built-in ATP detection structures; and (6) measure organism levels in the circulating fluid using a spectrometer or spectrophotometer. The results of these additional tests are forwarded to controller 52 which compares the test results to one or more baseline or other thresholds to determine if the circulating fluid has met the desired quality standards. Positive notification to the user of either meeting or not meeting the desired quality standards is provided. Further, the results of any one or more of these additional tests may be used by controller 52 for controlling any one or more of the valves 38, 62, and/or 64 in the manners described previously.

Figure 6:
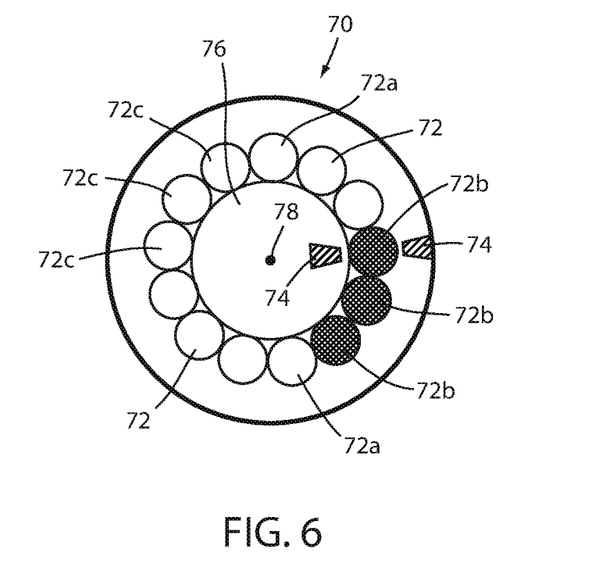
FIG. 6 is a plan view of a water quality assessment device that may be used in any of the thermal control systems disclosed herein.
Figure 7:
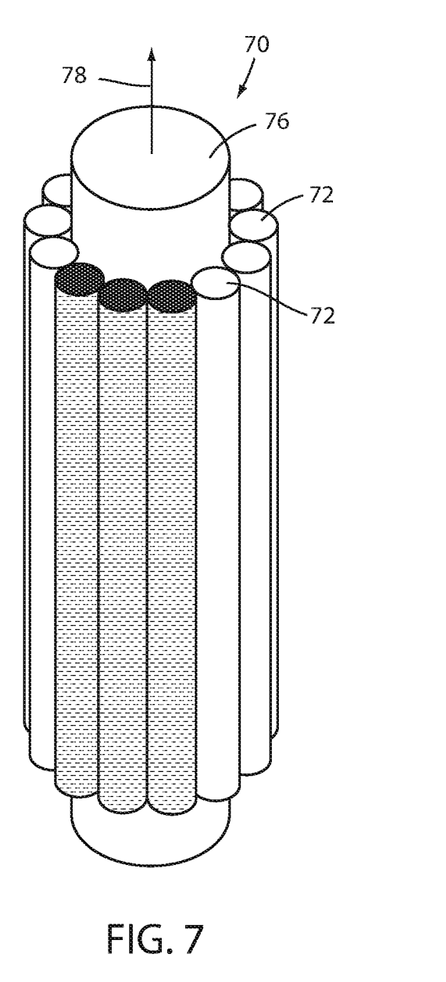
FIG. 7 is a perspective view of the water quality assessment device of FIG. 6.

In yet other alternative embodiments, any one or more of fluid quality monitors 46, 146, and/or 246 may be modified to include, either alone or in conjunction with the other components described above, a water (or other fluid) quality assessment device 70 of the type shown in FIGS. 6 and 7. Water quality assessment device 70 is built into the thermal control unit (22, 122, 222, or 322) and positioned at a location where samples of the circulating fluid can be automatically diverted at desired times and in quantities appropriate for assessment. Any suitable valve structure, control circuitry, and structural components necessary for carrying out this automatic delivery of fluid samples to device 70 and the subsequent automatic analysis of the assessment results may be used. Water quality assessment device 70 is included within fluid quality monitor 46 in some embodiments. In other embodiments, water quality assessment device 70 is separate from fluid quality monitor 46.

Water quality assessment device 70 includes a plurality of micro tubes 72 that are used to automatically test for the presence of contaminants in the circulating fluid. When the quality of the fluid is to be tested, one of the micro tubes 72 is filled with a sample of the circulating fluid and the height to which the fluid climbs in the vertical tube 72 due to the capillary effect is measured by a sensor 74. Sensor 74 may be an optical, video, or other type of sensor that is able to detect the height level of the fluid. The measured height is compared to a baseline measurement taken using clean fluid inside one of the micro tubes 72. In the example shown in FIG. 6, tubes 72a contain clean fluid, while tubes 72b contain fluid samples taken from the circulating fluid within the thermal control unit. Tubes 72c are empty and available for future assessments. If the height at which the tested fluid differs from the baseline height by more than a threshold, this is interpreted by controller 52 as indicating that the circulating fluid does not meet one or more cleanliness standards. Controller 52 then takes any of the previously mentioned actions. The height to which the sampled water travels via the capillary effect is changed by the presence of contaminants due to the contaminant's effect on the adhesion properties of the fluid. Thus, comparisons of the capillary height between a clean baseline sample and a current sample are used by controller 52 to assess the quality of the circulating fluid.

In some embodiments where capillary measurements are taken to assess the fluid quality, the tubes are coupled together around the perimeter of a central cylinder 76 that rotates on its longitudinal axis 78. Central cylinder 76 rotates on axis 78 when a new tube is filled with a sample, either to allow the tube to be filled and/or to move the tube into a position where its height can be automatically detected by the sensor 74. After measurement, the water sample may be automatically returned into circulation from the tube, or it may remain in the tube until manually emptied.

In an alternative variation of the water quality assessment device 70 shown in FIGS. 6 and 7, the micro tubes 72 are filled with fluid samples taken from the circulating fluid within the thermal control unit (22, 122, 222, or 322) and one or more other characteristics of the fluid are measured, either separately or in addition to the aforementioned evaluation of the height to which the fluid climbs in the micro tube 72. Such other tests include measuring the opacity of the water, the electrical conductivity of the water, and/or other tests. The results are automatically analyzed and used to take one or more of the responsive actions discussed above.

Figure 8:
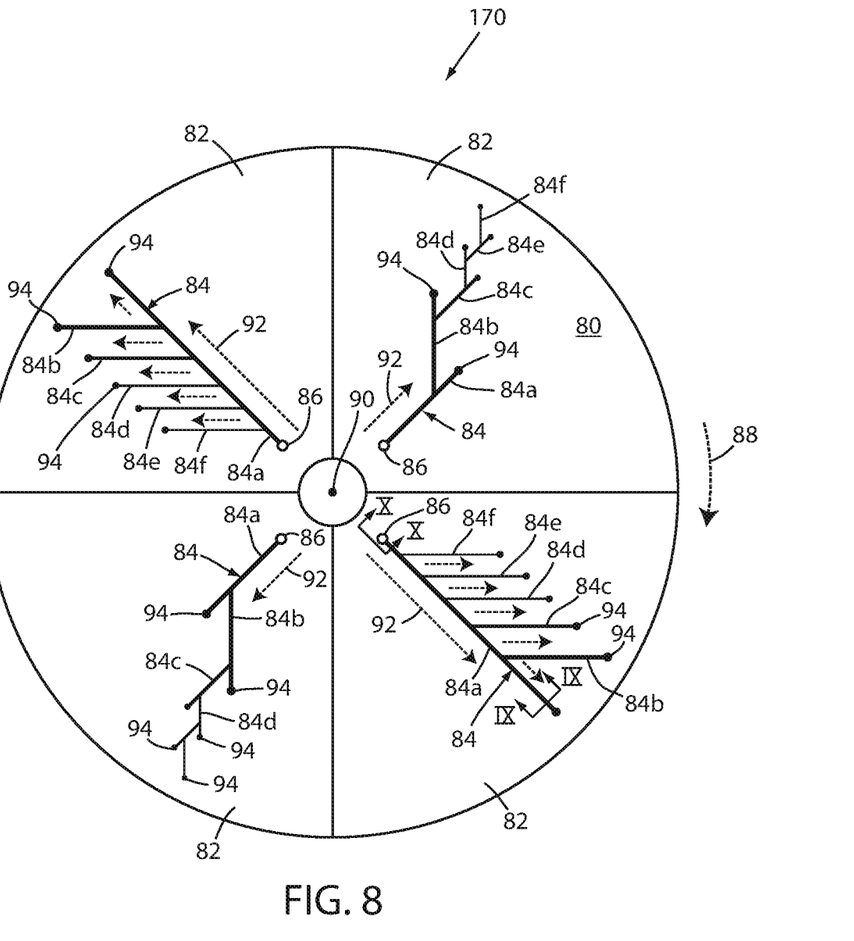
FIG. 8 is a plan view of an alternative water quality assessment disk that may be used in any of the thermal control systems disclosed herein.

An alternative water quality assessment device 170 is shown in FIG. 8 and, like water quality assessment device 70, may be used with any of the thermal control units disclosed herein. Assessment device 170, like assessment device 70, is built into the thermal control unit (either as part of fluid quality monitor 46, or separate therefrom) and includes corresponding mechanical structure that allows samples from the circulating fluid to be automatically delivered to assessment device 70 at the desired times and in the appropriate amounts. Assessment device 170 includes a disk 80 that is generally planar and circular shaped. Disk 80 is divided, in the illustrated embodiment, into four quadrants 82. A plurality of paths 84 are etched into disk 80 in each of the four quadrants 82.

Each path 84 is comprised of a main path 84a and a plurality of branches 84b. Many of the branches 84b include further branches 84c, which themselves may include even more branches 84d. Still more branches 84e, 84f, etc. may also be included. As the main path 84a branches into branches 84b, and as branches 84b further branch into branches 84c, the width of the paths get progressively smaller. That is, branches 84b are thinner than the main path 84a; branches 84c are thinner than branches 84b; branches 84c are thinner than 84d; and so on.

A sample of the circulating water is delivered to a fluid sample port 86 at the beginning of each of the paths 84. After the sample is delivered, disk 80 is spun about its central axis 90 in a direction indicated by arrow 88. The spinning is performed at a known and repeatable speed. Due to this spinning, the fluid samples delivered to sample ports 86 are subjected to centrifugal forces that urge the fluid radially outward in the direction indicated by arrows 92. This centrifugal force urges the fluid to travel down the main path 84a and through the various branches 84b, c, etc. The spinning of disk 80 continues for a predetermined amount of time.

After the spinning has stopped, measurements are taken of the amount of fluid and/or particles from within the fluid that have traveled to the end of each branch. That is, each branch includes a reservoir 94 at its end. Using any suitable sensing device (e.g. infrared, optical, ultrasonic, ultraviolet, conductive, and/or other types of sensors), measurements are taken of the amount of fluid and/or particles in the various reservoirs 94. These are compared to baseline measurements taken using fluid that is known to have been acceptably clean. Based on these measurements, controller 52 determines whether the circulating fluid from which the samples were taken is acceptable or if it needs cleaning/replacement. Controller 52 determines this by comparing the reservoir measurements to the baseline measurements and determining if the measurements are within an acceptable range of each other.

After a fluid sample has been tested using disk 80, the thermal control unit (22, 122, 222, or 322) may include a mechanism for automatically cleaning the disk 80 in order to allow future fluid samples to be tested using disk 80. Alternatively, disk 80 is not re-used, but a new disc is used for future fluid sample measurements. In some embodiments, the disks are comparable to conventional audio compact discs, but modified to include the structures discussed above (e.g. branches, reservoirs, fluid ports, etc.).

It will be understood that the particular branch patterns shown in FIG. 8 are but one illustrative layout for the paths 84 defined on disk 80. Other types of branching patterns may be used. In general, any branching pattern that includes a sufficient number of branches of varying widths may be used. Further, although not necessary, it may be advantageous to include the same branch pattern on opposite sides of the disk 80 so that the disc is balanced when spun. In other words, the branching pattern in the first and third quadrants 82 may be the same, while the branching pattern in the second and fourth quadrants may be the same, thereby helping to ensure better disc balance.

Figure 9:
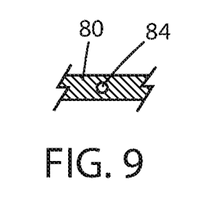
FIG. 9 is a cross sectional view of a portion of the water quality assessment disk of FIG. 8 taken along the line labeled IX-IX in FIG. 8.
Figure 10:
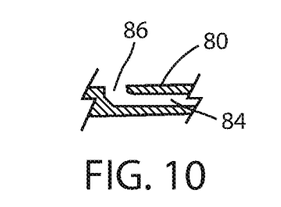
FIG. 10 is a cross sectional view of a portion of the water quality assessment disk of FIG. 8 taken along the line labeled X-X in FIG. 8.

It will also be understood that the paths 84 that are defined in disk 80 are internally defined therein. This is shown, for example, in FIG. 9. As can be seen therein, path 84 is encased within the body of disk 80. The only portion of path 84 that is open is the sample fluid ports 86, such as illustrated in FIG. 10. In some embodiments, the width of the smallest path 84 is approximately 0.2 microns, or smaller, so that only particles having smaller diameters are able to travel to the reservoir 94 at the end of the path. Other sized paths 84, however, may be used. The material of disk 80 may be any suitable material, including, but not limited to, polycarbonate.

By examining the amount of particulate matter at the end of one or more of the paths 84, controller 52 is able to determine the cleanliness of the circulating fluid and/or, the effectiveness of one or more of the filters in the thermal control unit, such as, but not limited to, filters 40, 140, and/or 240. Controller 52 uses this information in any of the manners, and for any of the purposes, discussed above with respect to thermal control units 22, 122, 222, and/or 322.

Any of the above embodiments of the thermal control units 22, 122, 222, and/or 322, may also be modified to take one or more automatic actions in response to determining that the quality of the circulating fluid has fallen below one or more predetermined thresholds. For example, in some embodiments, controller 52 is configured to automatically control a disinfectant dispenser (not shown) that adds disinfectant, and/or some other type of cleaning agent, to the circulating fluid when the fluid quality monitor detects that the fluid quality has fallen below one or more predetermined thresholds. The disinfectant can be any known and suitable disinfectant for cleaning the circulating fluid. In still other embodiments, controller 52 may change the state of one or more valves in response to unsatisfactory fluid quality wherein the changed valves direct fluid flow through a different fluid path that cleans the water (or other type of circulating fluid). The different fluid path includes an ultraviolet light in some embodiments that kills the living contaminants. In other embodiments, the different fluid path includes a filter or other structure that is impregnated with silver ions, or other bacteria-killing substances. In still other embodiments, such as that described above with respect to thermal control units 222 and 322, the alternate path may include only a low pore size filter (e.g. 0.2 microns or less) that cleans the circulating fluid via filtration. Still other manners of cleaning the circulating fluid may be used.

It will also be understood that any of the embodiments of thermal control unit 22 can be modified to include one or more additional filters 40, 140, and/or 240 that are positioned in parallel with their counterpart filter 40, 140, and/or 240. The additional filter that is arranged in parallel with its counterpart filter is used when the counterpart filter becomes clogged or otherwise no longer usable. When this is detected, controller 52 changes the state of one or more valves so that the circulating fluid stops flowing through the counterpart filter and instead flows through the additional filter. In this manner, if any filter becomes clogged or unusable, the thermal control unit is able to switch to a backup filter of the same type without having to shut down or otherwise interrupt the operation of the thermal control unit. When such a switch is made, the unit provides notification to the user via user interface 54, thereby giving the user ample opportunity to replace the clogged or unusable filter, while still allowing the thermal control unit 22 to function normally.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature, the thermal control unit comprising:
   a fluid outlet adapted to fluidly couple to a fluid supply line;
   a fluid inlet adapted to fluidly couple to a fluid return line;
   a fluid path coupling the fluid inlet to the fluid outlet;
   a pump for circulating fluid along the fluid path from the fluid inlet to the fluid outlet;
   a heat exchanger positioned along the fluid path and adapted to transfer heat to or from the circulating fluid;
   a filter adapted to filter the circulating fluid;
   a patient temperature probe port adapted to receive patient temperature readings from a patient temperature probe;
   a fluid quality monitor adapted to monitor a cleanliness of the circulating fluid and to issue a signal if the cleanliness of the circulating fluid falls below a threshold; and
   a controller adapted to use the patient temperature readings from the patient temperature probe port to control a temperature of the circulating fluid by controlling the heat exchanger; the controller further adapted to keep track of a rate at which particles accumulate in the filter and to use the rate to estimate a time in the future when the filter should be replaced.

2. The thermal control unit of claim 1 further including a user interface adapted to provide a visual indication to a user when the cleanliness of the circulating fluid is above the threshold.

3. The thermal control unit of claim 1 wherein the fluid quality monitor is adapted to monitor an amount of disinfectant in the circulating fluid.

4. The thermal control unit of claim 1 further including a valve having a first state in which the circulating fluid flows through the fluid quality monitor and a second state in which the circulating fluid is diverted from flowing through the fluid quality monitor.

5. The thermal control unit of claim 1 further including a dispenser adapted to dispense a cleaning agent in the circulating fluid, wherein the controller controls the dispenser based upon an output of the fluid quality monitor.

6. A thermal control unit for controlling a patient's temperature, the thermal control unit comprising:
    a fluid outlet adapted to fluidly couple to a fluid supply line;
    a fluid inlet adapted to fluidly couple to a fluid return line;
    a fluid path coupling the fluid inlet to the fluid outlet;
    a pump for circulating fluid along the fluid path from the fluid inlet to the fluid outlet;
    a heat exchanger positioned along the fluid path and adapted to transfer heat to or from the circulating fluid;
    a patient temperature probe port adapted to receive patient temperature readings from a patient temperature probe;
    a valve adapted to allow a portion of the circulating fluid to flow into an auxiliary path when the valve is open and to prevent all of the circulating fluid from flowing into the auxiliary path when the valve is closed;
    a first filter positioned in the auxiliary path and adapted to filter the circulating fluid; and
    a second filter positioned outside of the auxiliary path and adapted to filter the circulating fluid; and
    a controller adapted to use the patient temperature readings from the patient temperature probe port to control a temperature of the circulating fluid by controlling the heat exchanger, the controller further adapted to control the valve based upon a measurement of a cleanliness of the circulating fluid.

7. The thermal control unit of claim 6 wherein the second filter has a larger pore size than the filter positioned in the auxiliary path.

8. A thermal control unit for controlling a patient's temperature, the thermal control unit comprising:
    a fluid outlet adapted to fluidly couple to a fluid supply line;
    a fluid inlet adapted to fluidly couple to a fluid return line;
    a pump for circulating fluid along a primary fluid path from the fluid inlet to the fluid outlet;
    a first filter positioned in the primary fluid path and adapted to filter fluid flowing through the primary fluid path;
    a heat exchanger positioned along the primary fluid path and adapted to transfer heat to or from the circulating fluid;
    a patient temperature probe port adapted to receive patient temperature readings from a patient temperature probe;
    a valve;
    a second filter positioned along an auxiliary path;
    a bypass line separate from the auxiliary path and adapted to allow the circulating fluid to bypass the fluid supply line and the fluid return line; and
    a controller adapted to use the patient temperature readings from the patient temperature probe port to control a temperature of the circulating fluid by controlling the heat exchanger, the controller further adapted to control the valve such that fluid flows through the auxiliary path only in response to a specific event.

9. The thermal control unit of claim 8 wherein the specific event includes passage of an amount of time.

10. The thermal control unit of claim 8 wherein the specific event includes taking a measurement of cleanliness of the circulating fluid, the measurement taken at a location along the primary fluid path.

11. The thermal control unit of claim 8 wherein the specific event includes manual activation of a control on a user interface of the thermal control unit.

12. The thermal control unit of claim 8 wherein the second filter is part of a fluid quality monitor adapted to monitor a cleanliness of the circulating fluid.

13. The thermal control unit of claim 12 further comprising:
    a second valve adapted to selectively divert the circulating fluid toward a second auxiliary path; and
    a third filter positioned along the second auxiliary path.

14. The thermal control unit of claim 13 wherein the third filter has a pore size adapted to filter out particles having a size larger than 0.2 microns.

15. The thermal control unit of claim 13 wherein the controller is adapted to open the second valve so as to allow fluid to flow through the second auxiliary path in response to a cleaning action taken with respect to the circulating fluid.

16. The thermal control unit of claim 15 wherein the second auxiliary path is defined such that fluid flowing through the third filter must first flow through the second filter.

17. The thermal control unit of claim 15 wherein the controller is adapted to use a measurement associated with the third filter to determine if the cleaning action was effective or not.

* * * * *